(12) United States Patent
Rourke et al.

(10) Patent No.: US 6,207,596 B1
(45) Date of Patent: Mar. 27, 2001

(54) DISPOSABLE PREMOISTENED WIPE CONTAINING AN ANTIMICROBIAL PROTEASE INHIBITOR

(75) Inventors: Francis James Rourke, Sharonville, OH (US); Marc Frederic Richards, Corinth, KY (US); Scott Edward Osborne, Middletown, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/188,442

(22) Filed: Nov. 9, 1998

(51) Int. Cl.$^7$ .................................................. B32B 27/04
(52) U.S. Cl. ............................................................ 442/123
(58) Field of Search .............................................. 442/123

(56) References Cited

U.S. PATENT DOCUMENTS

| | | | |
|---|---|---|---|
| 3,786,615 | * 1/1974 | Bauer ........................................ | 53/21 |
| 3,935,862 | 2/1976 | Kraskin ................................. | 128/287 |
| 4,273,786 | 6/1981 | Kraskin ................................. | 424/319 |
| 4,505,924 | 3/1985 | Taylor et al. ......................... | 514/399 |
| 4,556,560 | 12/1985 | Buckingham ........................ | 424/145 |
| 4,619,942 | 10/1986 | Tidwell et al. ....................... | 514/415 |
| 4,714,563 | * 12/1987 | Kajs et al. ............................ | 252/107 |
| 4,781,974 | 11/1988 | Bouchette et al. ................... | 428/288 |
| 5,110,593 | 5/1992 | Benford ................................ | 424/401 |
| 5,230,897 | * 7/1993 | Griffin et al. ........................ | 424/449 |
| 5,417,981 | 5/1995 | Endo ..................................... | 424/486 |
| 5,629,081 | * 5/1997 | Richards et al. ..................... | 442/96 |
| 5,648,083 | 7/1997 | Blieszner et al. .................... | 424/402 |
| 5,686,088 | * 11/1997 | Mitra et al. .......................... | 424/404 |
| 5,871,763 | * 2/1999 | Luu et al. ............................. | 424/402 |
| 5,888,524 | 3/1999 | Cole ..................................... | 424/402 |
| 5,945,110 | * 8/1999 | Vianen et al. ........................ | 424/401 |

FOREIGN PATENT DOCUMENTS

| | | | |
|---|---|---|---|
| 0555116 | 8/1993 | (EP) . | |
| 0 564 307 | 10/1993 | (EP) ............................. | A61L/15/16 |
| 0 682 868 | 11/1995 | (EP) ............................. | A01N/59/12 |
| 0958833 | 11/1999 | (EP) . | |
| 2660552 | 10/1991 | (FR) ............................. | A61K/9/06 |
| 2675341 | 10/1992 | (FR) ............................. | A01N/37/52 |
| 2680448 | 2/1993 | (FR) ............................. | A01N/35/02 |
| 2714603 | 7/1995 | (FR) ............................. | A61K/31/16 |
| 04-182423 | 6/1992 | (JP) ............................. | A61K/7/50 |
| WO 92/20319 | 11/1992 | (WO) ........................... | A61K/7/00 |
| WO 97/16066 | 5/1997 | (WO) ........................... | A01N/25/04 |
| WO 9738735 | 10/1997 | (WO) . | |
| WO 9945974 | 9/1999 | (WO) . | |

OTHER PUBLICATIONS

U.S. application No. 08/926,532, Elder et al., filed Sep. 10, 1997.
U.S. application No. 08/926,533, Van Rijswijck et al., filed Sep. 10, 1997.
U.S. application No. 09/041,232, Rourke et al., filed Mar. 12, 1998.
U.S. application No. 09/041,266, Roe et al., filed Mar. 12, 1998.
U.S. application No. 09/186,902, Pung et al., filed Nov. 6, 1998.
Bernadette A. Mitchell, Melissa H. Brown, and Ronald A. Skurray, School of Biological Sciences, University of Sydney, New South Wales 2006, Australia QacA Multidrug Efflux Pump from *Staphylococcus aureus*: Comparative Analysis of Resistance to Diamidines, Biguanidines, and Guanylhydrazones Antimicrobial Agents and Chemotherapy, Feb. 1998, vol. 42, No. 2, pp. 475–477.
J. Chevalier and A. Crémieux, Laboratoire de Microbiologie, Hygiéne Microbienne, Immunologie, Faculté de Pharmacie, Marseille, France Comparative Study on the Antimicrobial Effects of Hexomedine and Betadine on the Human Skin Flora Journal of Applied Bacteriology, 1992, 73, pp. 342–348.
J.D. Geratz, Alan C. Whitmore, Department of Pathology, University of North Carolina School of Medicine and Michael C.–F. Cheng, Claude Piantadosi, Department of Medicinal Chemistry, University of North Carolina School of Pharmacy, Chapel Hill, North Carolina Diamidino–α,ω–diphenoxyalkanes, Structure–Activity Relationships for the Inhibition of Thrombin, Pancreatic Kallikrein, and Trypsin Journal of Medicinal Chemistry, 1973, vol. 16, No. 9, pp. 970–975.
Robert a. Briggaman, M.D., Department of Dermatology, University of North Carolina School of Medicine, Chapel Hill, North Carolina The Aromatic Diamidines International Journal of Dermatology, Apr. 1977, vol. 16, No. 3, pp. 155–162.
E.J. Dubovi, J.D. Geratz, S.R. Shaver and R.R. Tidwell, Departments of Pediatrics and Pathology, School of Medicine, University of North Carolina at Chapel Hill, Chapel Hill, North Carolina Inhibition of Respiratory Syncytial Virus–Host Cell Interactions By Mono–and Diamidines Antimicrobial Agents and Chemotherapy, Apr. 1981, vol. 19, No. 4, pp. 649–656.

* cited by examiner

*Primary Examiner*—Blaine Copenheaver
*Assistant Examiner*—Norca L. Torres
(74) *Attorney, Agent, or Firm*—Julia A. Glazer; Tara M. Rosnell

(57) ABSTRACT

A disposable wipe which comprises a substrate, an antimicrobial protease inhibitor, and a liquid. The antimicrobial protease inhibitor may be added directly to the substrate and/or added directly to the liquid. The antimicrobial protease inhibitor is capable of inhibiting deleterious fecal microorganisms and protease enzymes thereby aiding in the prevention of diaper dermatitis. The wipe may optionally include other ingredients examples of which include humectants, emollients, surfactants, fragrances, emulsifiers, and preservatives.

4 Claims, No Drawings

DISPOSABLE PREMOISTENED WIPE CONTAINING AN ANTIMICROBIAL PROTEASE INHIBITOR

FIELD OF THE INVENTION

The present invention relates to disposable premoistened wipes, and more particularly to disposable premoistened wipes which include an antimicrobial protease inhibitor effective at inhibiting deleterious fecal microorganisms and inhibiting protease enzymes.

BACKGROUND OF THE INVENTION

Premoistened wipes are well known in the art. Such wipes are also referred to as "wet wipes", "baby wipes" and "towelettes". Premoistened wipes include a nonwoven fibrous substrate which is wetted with a liquid prior to use. The substrate may include various combinations of cellulosic fibers, synthetic polymeric fibers such as polyester, polypropylene, polyethylene, and the like. The substrate may also include binders to hold the fibers together. The substrate is generally moistened with a liquid such as water. The liquid may include various other ingredients such as moistening agents or humectants, emollients, surfactants, emulsifiers, pH-adjusting agents, fragrances, powders, and the like.

Such premoistened wipes are commonly used to remove fecal matter and urine from the perineal area. Fecal matter and urine lead to perineal dermatitis. Perineal dermatitis, which includes diaper dermatitis, has been defined as contact dermatitis in the perineal area, including the perineum, buttocks, and the perineal, coccyx, and upper/inner thigh regions (Brown D. S., Serars M., Perineal Dermatitis: A Conceptual Framework, Ostomy/Wound Management 1993, 39 (7), 20–25). Diaper dermatitis is believed to be caused by the prolonged contact of the skin with body waste. The physical signs of diaper dermatitis may include one or a combination of erythema, swelling, oozing, visiculation, crusting, and scaling, with the possibility of excoriation, thickening, and hyperpigmentation over time (Brown).

The exact component or components of urine and feces responsible for diaper dermatitis has not been identified. Factors which have been suspected of causing diaper dermatitis include ammonia, moisture, urine pH, fecal microorganisms, and protease enzymes (such as those contained in fecal matter).

It is desirable to provide a premoistened disposable wipe that cleans and leaves behind a residue on the skin which inhibits the formation of diaper dermatitis.

It is also desirable to provide a premoistened disposable wipe which includes a single active agent capable of inhibiting the formation of diaper dermatitis by controlling both deleterious fecal microorganisms and protease enzymes.

One benefit of the present invention is the ability to inhibit formation of diaper dermatitis by utilizing a premoistened wipe containing an antimicrobial protease inhibitor. The antimicrobial protease inhibitor is capable of controlling deleterious fecal microorganisms and protease enzymes both of which are thought to be major contributors to the formation of diaper dermatitis.

A further benefit of the present invention is the ability of the premoistened wipe to both clean the skin and leave behind a residue of the antimicrobial protease inhibitor. Thus, inhibition of deleterious fecal microorganisms and protease enzymes continues even after the premoistened wipe is no longer in contact with the skin.

Prophetically, another benefit of the present invention is the ability to provide a regimen for maintaining or improving skin health utilizing the premoistened disposable wipe of this invention in conjunction with a disposable absorbent article such as a diaper.

SUMMARY OF THE INVENTION

The present invention is directed to a premoistened wipe capable of inhibiting deleterious fecal microorganisms and inhibiting protease enzymes. In one embodiment the premoistened wipe comprises a nonwoven fibrous substrate which includes from about 0.004% to 10% antimicrobial protease inhibitor by weight of dry fiber in the substrate and from about 0.5 grams to 8 grams of liquid per gram of dry fiber in the substrate.

The antimicrobial protease inhibitor exhibits an $IC_{50}$ on purified trypsin of less than about 1000 $\mu$M and a minimum inhibitory concentration for *Escherichia coli* of less than about 1000 $\mu$M.

The antimicrobial protease inhibitor is an aromatic diamidine selected from the group consisting of:

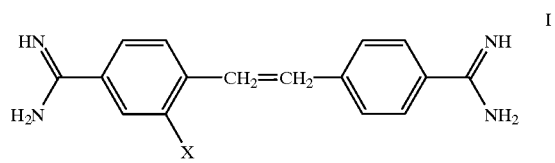

wherein X is H or OH, and

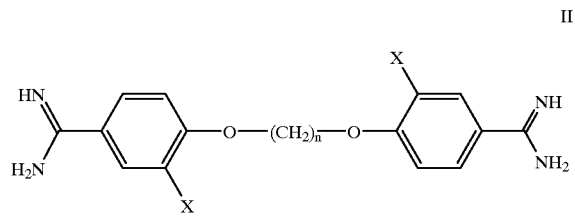

wherein n=3 to 12 and X is Cl, I, Br, F, or H.

The aromatic diamidine may be selected from the group consisting of pentamidine and hexamidine. A preferred hexamidine is hexamidine diisethionate. The aromatic diamidine may also be added directly to the substrate and or to the liquid.

When added to the liquid, the antimicrobial protease inhibitor comprises about 0.0005% to 10% of the liquid by weight. A solvent comprises about 50% of the liquid by weight. The solvent is selected from the group consisting of oil, alcohol, water, and mixtures thereof.

The liquid may also optionally include: one or more humectants comprising from about 0.5% to 10% of the liquid by weight; one or more emollients comprising from about 0.1% to 10% of the liquid by weight; one or more surfactants comprising from about 0.01% to 10% of the liquid by weight; and one or more preservatives comprising from about 0.01% to 1% of the liquid by weight.

The present invention also includes a skin care regimen for improving or maintaining the skin health of wearers of disposable absorbent articles in the wearer-contacting area, the skin care regiment comprises the steps of:

a) providing a premoistened wipe comprising a nonwoven fibrous substrate, the substrate including from about 0.5 grams to 8 grams of liquid per gram of dry fiber, the liquid further comprising:

i) a solvent wherein the solvent comprises at least about 50% of the liquid by weight, the solvent selected from the group consisting of oil, alcohol, water, and mixtures thereof; and ii) at least one antimicrobial protease inhibitor comprising from about 0.0005% to 10% of the liquid by weight;

b) wiping the wearer-contacting area of the skin with the premoistened wipe such that the antimicrobial protease inhibitor is transferred to the skin;

c) contacting the skin with a disposable absorbent article; and d) repeating steps a) through c).

DETAILED DESCRIPTION OF THE INVENTION

The premoistened wipe of the present invention comprises a substrate, an antimicrobial protease inhibitor, and a liquid. The antimicrobial protease inhibitor is capable of killing deleterious fecal microorganisms and inhibiting protease enzymes. As used herein, "premoistened" refers to the addition of a liquid to the substrate prior to use. The term "liquid" includes any material having a liquid phase, including but not limited to emulsions having a liquid phase. The substrate may be premoistened with liquid during manufacture or it may be premoistened with liquid after manufacture (e.g.; by the user at point of use).

The antimicrobial protease inhibitor may be added directly to the substrate or preferably mixed with the liquid. Alternatively, if desired the antimicrobial protease inhibitor may be added to the substrate both separately and as a component of the liquid. The preferred embodiment liquid includes an antimicrobial protease inhibitor capable of killing deleterious fecal microorganisms and inhibiting protease enzymes.

The Substrate

Referring to the components of the present invention in more detail, the premoistened wipe of the present invention includes a substrate comprising woven or nonwoven natural fibers, synthetic fibers, or mixtures thereof. Suitable synthetic fibers include fibers commonly used in textiles, such as but not limited to polyester, polyethylene, and polypropylene fibers.

Various methods can be used to form a suitable substrate for use in the present invention. Suitable methods for forming the substrate include but are not limited to spunbonding, meltblowing, carding, wet laying, and airlaying. Suitable techniques for binding the fibers of the substrate together include but are not limited to hydroentangling, needle punching, thermal bonding, ultrasonic bonding, and preferably chemical bonding.

Chemical bonding tends to be more economically favorable than other fiber binding techniques. Substrates in which the fibers are chemically bonded together also tend to be lower in density and hence have greater void volume than comparable substrates having fibers which are bonded together by other techniques. Hence, a substrate in which the fibers are chemically bonded together prophetically provides greater cleaning capacity than a comparable substrate having fibers bonded together by other techniques. Common chemical bonding agents include but are not limited to solvent based and resin based adhesives (e.g.; latex, etc.).

Examples of other techniques which may be used in the manufacturing of substrates suitable for the present invention include but are not limited to surface treating and laminating.

In one embodiment, the substrate can be an airlaid nonwoven fibrous substrate comprising a combination of natural fibers, staple length synthetic fibers and a latex adhesive binder. The dry fibrous substrate can be about 20% to 80% by weight wood pulp fibers, about 10% to 60% by weight staple length polyester fibers, and about 10% to 25% by weight binder.

The dry, fibrous substrate can have a grammage of between about 40 to 100 grams per square meter. The density of the dry substrate, is preferably less than about 0.2 grams per cubic centimeter. The density of the dry substrate is calculated by dividing the grammage of the dry substrate by the thickness of the dry substrate, in consistent units. The thickness of the dry substrate is measured using a circular foot having an area of 2 square inches and which provides a confining pressure of about 95 grams per square inch. In one embodiment, the dry substrate has a grammage of about 64 grams per square meter, a thickness of about 0.06 cm, and a density of about 0.11 grams per cubic centimeter.

In one embodiment, the dry fibrous substrate can comprise at least about 50% by weight wood pulp fibers, and more preferably at least about 70% by weight wood pulp fibers. One particular airlaid nonwoven fibrous substrate which is suitable for use in the present invention comprises about 75% by weight Southern softwood Kraft wood pulp fibers having an average fiber length of about 2.6 mm; about 12% by weight polyester fibers having a denier of about 1.35 grams per 9000 meters of fiber length and a staple length of about 0.85 inch; and about 13% by weight of a binder composition comprising a styrene butadiene copolymer. The preferred styrene butadiene copolymer has a styrene to butadiene ratio of about 45 parts styrene to 55 parts butadiene. A latex adhesive suitable for making the binder composition is ROVENE 5550 (containing about 50 weight percent solids of styrene butadiene copolymer) available from Mallard Creek Polymers of Charlotte, N.C.

In one embodiment the substrate of the present invention is formed by air laying a blend of natural and synthetic fibers to form a fibrous web, spraying water on the web, and then embossing the web. A latex adhesive binder is then applied to the web, followed by drying and curing of the latex adhesive binder in an oven. The nonwoven web is then premoistened with a liquid. An example of such a premoistened web is PAMPERS BABY FRESH brand baby wipes marketed by the instant assignee.

Other webs and methods of making webs suitable for use in the present invention include but are not limited to those described in the following patents the disclosures of which are incorporated herein by reference: U.S. Pat. No. 3,862,472 issued Jan. 28, 1975 to Norton et al.; U.S. Pat. No. 3,905,863, issued Sep. 16, 1975 to Ayers; U.S. Pat. No. 3,974,025 issued Aug. 10, 1976 to Ayers; U.S. Pat. No. 3,918,126 issued Nov. 11, 1975 to Wood; U.S. Pat. No. 3,982,302 issued Sep. 28, 1976 to Vaalburg; U.S. Pat. No. 4,004,323 issued Jan. 25, 1977 to Gotchel et al.; U.S. Pat. No. 4,014,635 issued Mar. 29, 1977 to Kroyer; U.S. Pat. No. 4,057,669 issued Nov. 8, 1977 to McConnell; U.S. Pat. No. 4,064,600 issued Dec. 27, 1977 to Gotchel et al.; U.S. Pat. No. 4,074,393 issued Feb. 21, 1978 to Hicklin et al.; U.S. Pat. No. 4,097,965 issued Jul. 4, 1978 to Gotchel et al.; U.S. Pat. No. 4,130,915 issued Dec. 26, 1978 to Gotchel et al.; U.S. Pat. No. 4,144,619 issued Mar. 20, 1979 to White et al.; U.S. Pat. No. 4,176,426 issued Dec. 4, 1979; U.S. Pat. No. 4,176,427 to Neuenschwander; U.S. Pat. No. 4,191,609 issued Mar. 4, 1980 to Trokhan; U.S. Pat. No. 4,207,367 issued Jun. 10, 1980 to Baker, Jr.; U.S. Pat. No. No. 4,296,161 issued Oct. 20, 1981 to Kaiser et al., U.S. Pat. No.

4,309,469 issued Jan. 5, 1982 to Varona; U.S. patent application Ser. No. 08/915,349 filed Aug. 22, 1997 (pending); and U.S. Pat. No. Application Serial No. 09/132,833 filed Aug. 12, 1998 (abandoned).

Antimicrobial Protease Inhibitor

An antimicrobial protease inhibitor effective for controlling deleterious fecal microorganisms and protease enzymes may be added directly to the substrate or preferably to the liquid. When added directly to the substrate, the antimicrobial protease inhibitor is added to the substrate in an amount of about 0.004% to 10% active antimicrobial protease inhibitor by weight of dry fiber in the substrate, preferably in the amount of about 0.04% to 5% active antimicrobial protease by weight of dry fiber in the substrate, and more preferably in the amount of about 0.08% to 2% active antimicrobial protease inhibitor by weight of dry fiber in the substrate.

Preferably the antimicrobial protease inhibitor is an aromatic diamidine wherein the aromatic diamidine is selected from the group consisting of:

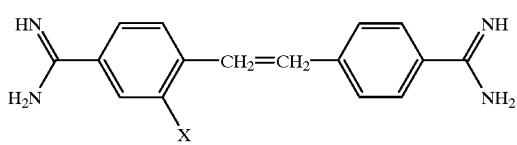

I wherein X is H or OH, and

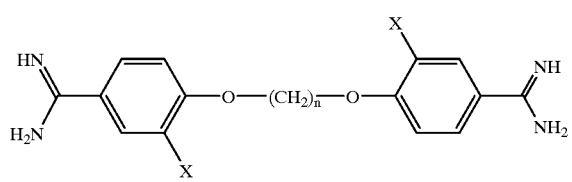

II wherein n=3 to 12 and X is Cl, I, Br, F, or H.

More preferably, the antimicrobial protease inhibitor is an aromatic diamidine selected from the group consisting of pentamidine, hexamidine, and mixtures thereof. Most preferably the antimicrobial protease inhibitor is hexamidine diisethionate.

A suitable hexamidine diisethionate is ELESTAB HP100 available from Laboratoires Serobiologiques S. A. of Pulnoy, France.

Liquid

The liquid of the premoistened wipe of the present invention is comprised of at least one solvent, and preferably an antimicrobial protease inhibitor(s). A nonlimiting list of other optional components which may be included in the liquid are: a humectant(s), an emollient(s), a surfactant(s), a fragrance(s), a fragrance emulsifier(s), and/or a preservative (s).

As used herein, "% by weight" refers to the quantity of active component by weight contained in the liquid as a percentage of the total weight of the liquid.

The premoistened wipe is made by wetting the dry substrate with about 0.5 gram to 8 grams of liquid per gram of dry fiber in the substrate and preferably from about 1 grams to 6 grams of liquid per gram of dry fiber in the substrate.

Solvent(s)

Solvents useful in the liquid of the present invention include oil, alcohol, and preferably water. Mixtures of these solvents may also be used. The solvent comprises at least about 50% of the liquid by weight, preferably at least about 75% of the liquid by weight, and more preferably at least about 90% of the liquid by weight.

Antimicrobial Protease Inhibitor(s)

When added to the liquid, the antimicrobial protease inhibitor comprises from about 0.0005% to 10% of the liquid by weight, preferably from about 0.005% to 5% of the liquid by weight, and more preferably from about 0.01% to 2% of the liquid by weight.

Optional Components of the Liquid

Humectant(s):

The liquid of the present invention may optionally contain one or more humectants. As used herein, "humectant" refers to a hygroscopic material that functions to draw water into the stratum corneum to hydrate the skin. The water may come from the dermis or from the atmosphere. Suitable humectants include, but are not limited to glycerin, sorbitol, phospholipids, and preferably propylene glycol. The humectant may comprise from about 0.5% to 10% of the liquid by weight, preferably from about 1% to 5% of the liquid by weight, and more preferably from about 1.5% to 3.5% of the liquid by weight. A suitable propylene glycol is available from Dow Coming of Midland, Mich.

Emollient(s):

The liquid may optionally include one or more emollients. As used herein, "emollient" refers to a material that softens, soothes, supples, coats, lubricates, or moisturizes the skin. Emollients include, but are not limited to conventional lipid material (i.e.; fats, waxes), polar lipids (lipids that have been hydrophylically modified to render them more water soluble), silicones, hydrocarbons, and other solvent materials.

Emollients useful in the present invention can be petroleum based, fatty acid ester based, alkyl ethoxylate based, fatty acid ester ethoxylate based such as polyethylene glycol (e.g.; lanolin, etc.), fatty alcohol based, polysiloxane based, mucopolysaccharides, or mixtures thereof. The emollient may comprise from about 0.01% to 10% of the liquid by weight, preferably from about 0.1% to 5% of the liquid by weight, and more preferably from about 0.3% to 2% of the liquid by weight. A preferred emollient is LANETO 50 (a 50% solid lanolin) available from Rita Corporation of Woodstock, Ill.

Surfactant(s):

The liquid may optionally include one or more surfactants. As used herein, "surfactant" refers to a material which changes the surface properties of a liquid or solid by reducing the surface tension at the interface with the liquid or solid. Classes of surfactants include but are not limited to nonionic surfactants, anionic surfactants, cationic surfactants, amphoteric surfactants, preferably zwitterionic surfactants, and mixtures thereof. The surfactant may comprise from about 0.01% to 10% of the liquid by weight, preferably from about 0.1% to 5% of the liquid by weight, and more preferably from about 0.3% to 2% of the liquid by weight.

A preferred zwitterionic surfactant is octyliminodipropionate, available as MACKHAM ODP available from McIntyre Group Ltd. of University Park, Ill.

Fragrance(s):

The liquid may optionally include one or more fragrances. Fragrance components, such as perfumes, include, but are not limited to water insoluble oils, including essential oils.

The fragrance may comprise from about 0.005% to 0.5% of the liquid by weight, preferably from about 0.01% to 0.1% of the liquid by weight, and more preferably from about 0.02% to 0.06% of the liquid by weight.

Fragrance Emulsifier(s):

The liquid may optionally include one or more fragrance emulsifiers. A fragrance emulsifier, also known as a fragrance solubilizer, reduces the tendency of the water insoluble fragrance component to precipitate out of the liquid. Examples of fragrance emulsifiers include, but are not limited to, alcohols such as ethanol, isopropanol, benzyl alcohol, and phenoxyethanol; any high HLB emulsifier (i.e.; HLB greater that about 13) including but not limited to highly ethoxylated acids and alcohols and preferably polysorbate. The fragrance emulsifier may comprise from about 0.01% to 5% of the liquid by weight, preferably from about 0.1% to 2% of the liquid by weight, and more preferably from about 0.2% to 0.8% of the liquid by weight.

A suitable fragrance emulsifier is polysorbate 20 available as TWEEN 20 from Imperial Chemical Company (ICI) of New Castle, Del.

Preservative(s):

The liquid may optionally include one or more preservatives. Preservatives are used in order to prevent the growth of microorganisms in the liquid and/or the substrate. Suitable preservatives include but are not limited to methylparaben, propylparaben, and 2-Bromo-2-nitropropane-1,3-diol. Methylparaben may comprise from about 0.01% to 1% of the liquid by weight. Propylparaben may comprise from about 0.005% to 0.5% of the liquid by weight. The 2-Bromo-2-nitropropane-1,3-Diol may comprise from about 0.005 % to 0.2% of the liquid by weight.

A suitable methylparaben is a National Formulary grade of methylparaben available from Acme Hardesty Company of Jenkintown, Pa. A suitable propylparaben is a National Formulary grade of propylparaben also available from Acme Hardesty Company. A suitable 2-Bromo-2-nitropropane-1, 3-diol is BRONOPOL® available from Inolex Chemical Company of Philadelphia, Pa.

Other liquids with which the substrate can be moistened are described in the following patent documents which are incorporated herein by reference: U.S. Pat. No. 4,941,995 issued Jul. 17, 1990 to Richards et al.; U.S. Pat. No. 4,904,524 issued Feb. 27, 1990 to Yoh; U.S. Pat. No. 4,772,501 issued Sep. 20, 1988 to Johnson et al.; U.S. Pat. No. 4,556,560 issued Dec. 3, 1985 to Buckingham; and U.S. Pat. No. 5,648,083 issued Jul. 15, 1997 to Bliezner et al.

Techniques for Combining Substrate, Antimicrobial Protease Inhibitor, and Liquid Techniques for combining wipes substrates with a liquid composition, and their packaging are well known in the art and applicable to the present invention. In general, the antimicrobial protease inhibitor may be added to the substrate in the form of a dry powder or a solution. It may be added to the substrate separate from the liquid. Alternatively, it may be added to the substrate as a component of the liquid or it may be added both separately and as a component of the liquid.

Examples of techniques well known in the art which may be used to apply the antimicrobial protease inhibitor and/or liquid to the substrate include but are not limited to immersing, embossing, dipping, spraying, extruding, coating, printing, impregnation, and the like. Techniques useful for combining substrates with compositions suitable for use in the present invention are described in the following patents the disclosures of which are incorporated herein by reference: U.S. Pat. No. 4,189,896 issued Feb. 26, 1980 to Kohlbach et al. and U.S. Pat. No. 4,135,024 issued Jan. 16, 1979 to Callahan et al.

EXAMPLES

A. Method of Making A Liquid Composition Which Contains No Antimicrobial Protease Inhibitor (i.e.; "control")

An aqueous liquid control composition was made by the following procedure:

Premix 1:

A first premix was made by blending the following components together: 15 grams of propylene glycol, 2 g of methylparaben, and 0.3 g of propylparaben.

Premix 2:

A second premix was made by blending the following components together: 2 grams of Polysorbate 20 and 0.375 g of fragrance.

Premix 1 was added to 970 g of distilled water. To this mixture was added 0.500 g of BRONOPOL®, 5 g of octyliminodipropionate, and 5 g of LANETO 50 (i.e.; PEG-75 lanolin). Premix 2 was then added to this mixture.

B. Method of Making A Liquid Composition Containing an Antimicrobial Protease Inhibitor A liquid containing a 1% antimicrobial protease inhibitor (i.e.; "hexamidine") was made by the following procedure:

Premix 1:

A first premix was made by blending the following components together: 15 g of propylene glycol, 2 g of methylparaben, and 0.3 g of propylparaben.

Premix 2:

A second premix was made by blending the following components together: 2 g of Polysorbate 20 and 0.375 g of fragrance.

10 g of hexamidine diisethionate was added to 960 g of distilled water. Premix 1 was then added to this. To this mixture was added 0.500 g of BRONOPOL®, 5 g of octyliminodipropionate, and 5 g of PEG-75 lanolin. Premix 2 was then added.

C. Test Methods

Enzyme Inhibition Assays:

Standard in vitro assays for determining enzyme activity, and inhibition of enzyme activity, are well known. The reagents used to conduct these tests are generally commercially available. In general, a simple system comprises an enzyme-specific substrate which, when hydrolyzed by the enzyme, produces a colored product. The activity of the enzyme is measured spectrophotometrically as the degree of development of the colored product (i.e.; the rate of color change) over a predetermined time period.

Inhibition of enzyme activity is exhibited as a measurable decrease in the rate of color change over the same period in the presence of an enzyme inhibitor.

The inhibitory activity of an enzyme inhibitor may be calculated according to the following equation:

$$IC_{50} = [I]/[(v/v_i) - 1],$$

where $IC_{50}$ refers to the minimum concentration of enzyme inhibitor required to inhibit 50% of the enzyme, [I] is the enzyme inhibitor concentration tested, v is the rate of substrate cleavage by the enzyme in the absence of enzyme inhibitor and $v_i$ is the rate of substrate cleavage in the presence of enzyme inhibitor.

The following methods may be used to determine the inhibitory activity of an enzyme inhibitor effective at inhibiting protease enzymes known to exist in feces.

In the methods, v and $v_i$ are measured as the change in absorbency (optical density, OD) at a given wavelength/time (e.g., minutes). The methods utilize trypsin buffer made by the following procedure: 60.55 g of TRIS and 22.20 grams of $CaCl_2$ are dissolved in 0.9 ml of distilled water. The pH of this solution is adjusted to 8.2 with hydrochloric acid. This is then diluted with water to a final volume of 1 liter to form a solution of 500 mM TRIS and 200 mM $CaCl_2$.

1. Purified Protease Methods

The purified protease methods utilize purified trypsin made by the following procedure: 0.124 mg of human pancreatic trypsin (having a molecular weight of 22,000) are dissolved in 0.564 ml of 0.001N HCl to form a 10 $\mu$M stock solution. This solution is diluted 1:263.2 with distilled water (i.e.; 5 $\mu$l of trypsin stock and 1.311 ml of distilled water) to give a 38 nM trypsin solution. Suitable human pancreatic trypsin for this purpose is available as catalogue No. T6424 from Sigma Aldrich Company of St. Louis, Mo.

a. Method of Evaluating Efficacy of Protease Inhibitors in Purified Trypsin

This method is used to test the efficacy of a protease inhibitor against purified trypsin.

A substrate comprised of 46.5 g of N-carbobenzyloxy-arginine-p-nitroanilide (having a molecular weight of 464.9) is dissolved in 1.0 ml of dimethyl sulfoxide (hereinafter referred to as "DMSO") to form a 100 $\mu$M stock solution. This stock solution is diluted 1:25 in distilled water (i.e.; 20 $\mu$l of stock solution and 0.48 ml of distilled water) to provide a 4 mM substrate solution. A suitable substrate is available as catalogue No. C4893 from Sigma Aldrich Company of St. Louis, Mo.

Serial dilutions of a protease inhibitor are made using distilled water. A 50 $\mu$l aliquot of each serial dilution of protease inhibitor to be evaluated is added to a microcuvette containing 0.020 ml of trypsin buffer and 0.105 ml of purified trypsin. The microcuvette is incubated at 25° C. for 10 minutes.

After incubating, 0.025 ml of the 4 mM N-carbobenzyloxy-arginine-p-nitroanilide substrate solution is added to the microcuvette. The microcuvette is mixed. The absorbency of the mixture is then measured at a wavelength of 405 nm over a period of 10 minutes at a temperature of 25° C.

b. Method of Evaluating the Efficacy of Liquid Compositions Containing Protease Inhibitors in Purified Trypsin This method is used to test the efficacy of a liquid composition containing a protease inhibitor against purified trypsin. For this purpose, a liquid composition containing protease inhibitor and made according to Method B above is used.

A 0.05 ml aliquot of the liquid composition containing protease inhibitor made according to Method B above is serially diluted with a liquid composition containing no protease inhibitor made according to Method A above. A 50 $\mu$l aliquot of each serial dilution of the liquid composition containing protease inhibitor to be evaluated is added to a microcuvette containing 0.020 ml of trypsin buffer and 0.105 ml of purified trypsin. The microcuvette is incubated at 25° C. for 10 minutes.

After incubating, 0.025 ml of the 4 mM N-carbobenzyloxy-arginine-p-nitroanilide substrate solution is added to the microcuvette. The microcuvette is mixed. The absorbency of the mixture is then measured at a wavelength of 405 nm over a period of 10 minutes at a temperature of 25° C. using a spectrophotometer.

The antimicrobial protease inhibitor(s) comprising the premoistened wipe of the present invention exhibits an $IC_{50}$ on purified trypsin of less than about 1000 $\mu$M, preferably less than about 500 $\mu$M, and more preferably less than about 100 $\mu$M.

2. Fecal Protease Methods

The following is a general description of a method for obtaining a sample of feces suitable for use in Fecal Protease methods.

For purposes of establishing a positive control to ensure that the pooled sample feces exhibit the requisite enzyme activity for assessing protease inhibitory activity, the following procedure is followed for each of the Fecal Protease Methods. Pooled infant feces (at least five different samples) are collected in a manner to keep them free of urine and contamination and mixed with distilled water to obtain a weight by weight (w/w) mixture (e.g., 1:50 w/w). This mixture is then mixed thoroughly to obtain a homogeneous suspension by homogenization or sonication.

The pooled fecal suspension is used as a source of protease activity as described below and will exhibit a rate of substrate turnover in the absence of inhibitor in the range of about 0.005 $OD_{405}$ per minute to 0.020 $OD_{405}$ per minute. (Also, to ensure complete linearity the final absorbency should not exceed 1.5 $OD_{405}$ units). If the activity of the pooled infant feces is outside this range, it is not possible to accurately determine $IC_{50}$ values for putative protease inhibitors. However, the range of enzyme activity may be adjusted by increasing or decreasing the dilution factor accordingly for each enzyme. If this is not possible, a different group of subjects should be used to obtain the sample pool.

a. Method of Evaluating Efficacy of Protease Inhibitors in Fecal Trypsin

This method is used to test the efficacy of a protease inhibitor against the trypsin activity in feces.

A substrate comprised of 14 g of N-carbobenzyloxy-arginine-p-nitroanilide is added to 0.5 ml of methanol to make a 60 mM stock solution. The stock solution is diluted 1:20 with distilled water (i.e.; 0.05 ml of stock solution and 0.95 ml of distilled water) to form a 2 mM substrate solution.

Serial dilutions of a protease inhibitor are made using distilled water. A 0.7 ml aliquot of each dilution of protease inhibitor to be evaluated is added to a microcuvette. To this is added, 0.1 ml of trypsin buffer and 0.1 ml of a 3 mM solution of substrate. The microcuvette is mixed by inversion and incubated at 25° C. for 5 minutes.

A volume of 0.1 mL of fecal suspension is added to the microcuvette and mixed. The absorbency of the mixture at 490 nm is measured with the spectrophotometer. The absorbency at 490 nm represents a correction factor for the background absorbency due to the particulate fecal material (i.e., "interference"). The absorbency of the mixture at 405 nm is then measured with the spectrophotometer over a period of 5 minutes at 25° C. These absorbency readings are subtracted from the absorbency reading at 490 nm in order to correct for any background interference. The corrected absorbency readings are then used to calculate the rate of substrate cleavage per minute.

The antimicrobial protease inhibitor(s) comprising the premoistened wipe of the present invention exhibits an $IC_{50}$ on fecal trypsin of less than about 1000 $\mu$M, preferably less than about 500 $\mu$M, and more preferably less than about 100 $\mu$M.

3. Method for Determining the Activity of Antimicrobial Agents:

This method is used to determine the antimicrobial activity of antimicrobial agents. The antimicrobial activity of an antimicrobial agent is tested according to the National Committee for Clinical Laboratory Standards ("NCCLS") Methods. The NCCLS Dilution Antimicrobial Susceptibility Test for Bacteria Which Grow Aerobically is used (i.e.; NCCLS Document M7-A2, 1990).

Serial two-fold dilutions of the antimicrobial agent are made in trypticase soy broth in a microtiter plate (in the case of hexamidine diisethionate a 1000 $\mu$M starting concentration is recommended). Microorganism inocula are prepared by harvesting colonies from agar plates into saline and adjusting the optical density of the solution to be equivalent to the 0.5 McFarland standard. Each microorganism suspension is diluted 1:10 and 10 microliters of the suspension added to each microtiter well.

The microtiter plates are sealed and incubated for 24 hours at 37° C. The highest dilution of the antimicrobial agent preventing growth is recorded as the minimal inhibitory concentration ("MIC").

The antimicrobial protease inhibitor(s) comprising the premoistened wipe of the present invention exhibits a minimum inhibitory concentration for *Escherichia coli* of less than about 1000 $\mu$M, preferably less than about 500 $\mu$M, and more preferably less than about 100 $\mu$M.

EXAMPLES

The protease inhibitory activity and antimicrobial activity of an antimicrobial protease inhibitor, hexamidine diisethionate, were evaluated.

Example 1

Referring to Table I, the inhibitory activity of hexamidine diisethionate (reported as $IC_{50}$) is shown.

Referring to Table I, column 1, the inhibitory activity of hexamidine diisethionate against fecal trypsin was evaluated according to Method 2a above (i.e.; "Method of Evaluating Efficacy of Protease Inhibitors in Fecal Trypsin).

Referring to Table I, column 2, the inhibitory activity of hexamidine diisethionate against purified trypsin was evaluated according to Method 1 a above (i.e.; "Method of Evaluating Efficacy of Protease Inhibitors in Purified Trypsin).

Referring to Table I, column 3, the inhibitory activity of a liquid composition containing hexamidine diisethionate against purified trypsin was evaluated according to Method 1 b above (i.e.; "Method of Evaluating the Efficacy of Liquid Compositions Containing Protease Inhibitors in Purified Trypsin").

TABLE I

PROTEASE INHIBITORY ACTIVITY
OF HEXAMIDINE DIISETHIONATE

| FECAL TRYPSIN $IC_{50}$ ($\mu$M) | PURIFIED TRYPSIN $IC_{50}$ ($\mu$M) | PURIFIED TRYPSIN (INHIBITORY ACTIVITY OF LIQUID COMPOSITION CONTAINING HEXAMIDINE DIISETHIONATE) $IC_{50}$ ($\mu$M) |
|---|---|---|
| 2.3 | 2.5 | 2.8 |

Example 2

Referring to Table II, the antimicrobial activity of hexamidine diisethionate on three different microorganisms is shown. For purposes of this example, hexamidine diisethionate was diluted with distilled water and evaluated according to Method 3 above.

TABLE II

ANTIMICROBIAL ACTIVITY OF HEXAMIDINE DIISETHIONATE

| Organism | ATCC Strain No. | Minimal Inhibitory Concentration ($\mu$M) |
|---|---|---|
| *Escherichia coli* | 25922 | 53 |
| *Staphylococcus aureus* | 25923 | 3 |
| *Candida Albicans* | 10231 | 13 |

Example 3

Referring to Table III, the antimicrobial inhibitory activity of a liquid composition containing no antimicrobial protease inhibitor was compared to the antimicrobial inhibitory activity of a liquid composition containing an antimicrobial protease inhibitor. The antimicrobial protease inhibitor chosen for this evaluation was hexamidine diisethionate.

The antimicrobial inhibitory activity of hexamidine diisethionate is reported as the minimal inhibitory concentration ("MIC") of hexamidine diisethionate required to inhibit a particular organism. Referring to Table III, column 1 indicates the particular microorganism against which the antimicrobial inhibitory activity of hexamidine diisethionate was evaluated. Referring to Table III, column 2, the ATCC Strain identification No. for the microorganism listed in column 1 is shown.

Referring to Table III, column 3, the antimicrobial inhibitory activity of a liquid composition containing no antimicrobial protease inhibitor is shown. The liquid composition was made according to Methods A and C3 above.

Referring to Table III, column 4, the antimicrobial inhibitory activity of a liquid composition containing hexamidine diisethionate is shown. The liquid composition was made according to Methods B and C3 above.

TABLE III

Minimal Inhibitory Concentration of Liquid Composition

| Organism | ATCC Strain No. | Control | Liquid Composition Containing Hexamidine Diisethionate |
|---|---|---|---|
| *Staphylococcus aureus* | 25923 | 1:128 | 1:262,144 |
| *Enterococcus faecalis* | 29212 | 1:64 | 1:524:288 |
| *Pseudomonas aeruginosa* | 27853 | 1:128 | 1:512 |
| *Escherichia coli* | 25922 | 1:128 | 1:1024 |
| *Staphylococcus epidermidis* | 12228 | 1:128 | 1:524,288 |
| *Proteus vulgaris* | 13315 | 1:256 | 1:1024 |
| *Candida albicans* | 10231 | 1:64 | 1:32768 |

Skin Care Regimen

For wearers of disposable absorbent articles such as diapers, training pants, adult incontinence briefs, sanitary napkins, etc., the wipe of the present invention may prophetically be used in combination with the disposable absorbent article as part of a skin care regimen wherein skin health in the wearer-contacting area is maintained or improved by using the combination. As used herein, "wearer-contacting area" refers to the area of the wearer's skin contacted by the disposable absorbent article during use.

The regimen comprises the repetition of the following steps:

a) wiping the wearer-contacting area of the skin with the wipe of the present invention such that the antimicrobial protease inhibitor is transferred to the skin; and b) contacting the skin with the disposable absorbent article.

Especially preferred absorbent articles for this purpose are disclosed in U.S. Ser. No. 08/926,532 filed Sep. 10, 1997 (pending), U.S. Ser. No. 08/926,533 filed Sep. 10, 1997 (pending), U.S. Ser. No. 09/041,232 filed Mar. 12, 1998 (abandoned), and U.S. Ser. No. 09/041,266 filed Mar. 12, 1998 (pending), the disclosures of which are incorporated herein by reference.

Other absorbent articles suitable for use with the wipe of the present invention include but are not limited to those described generally in: U.S. Pat. No. 3,860,003 issued on Jan. 14, 1975 to Buell; U.S. Pat. No. 4,342,314 issued on Aug. 3, 1982 to Radel et al.; U.S. Pat. No. 4,463,045 issued on Jul. 31, 1984 to Ahr et al.; U.S. Pat. No. 4,556,146 issued on Dec. 3, 1985 to Swanson et al.; U.S. Pat. No. B1 4,589,876 certificate issued on Apr. 27, 19 to Van Tilburg; U.S. Pat. No. 4,687,478 issued Aug. 18, 1987 to Van Tilburg; U.S. Pat. No. 4,950,264 issued on Aug. 21, 1990 to Osborn, III; U.S. Pat. No. 5,009,653 issued on Apr. 23, 1991 to Osborn, III; U.S. Pat. No. 5,151,092 issued on Sep. 9, 1992 to Buell; U.S. Pat. No. 5,171,236 issued Dec. 15, 1992 to Dreier et al.; U.S. Pat. No. 5,221,274 issued Jun. 22, 1993 to Buell; U.S. Pat. No. 5,267,992 issued on Dec. 7, 1993 to Van Tilburg; U.S. Pat. No. 5,306,266 issued Apr. 26, 1994 to Freeland; U.S. Pat. No. 5,397,318 issued on Mar. 14, 1995 to Dreier; U.S. Pat. No. 5,514,121 issued May 7, 1996 to Roe et al.; U.S. Pat. No. 5,540,671 issued on Jul. 30, 1996 to Dreier; U.S. Pat. No. 5,554,142 issued Sep. 10, 1996 to Dreier et al.; U.S. Pat. No. 5,554,145 issued Sep. 9, 1996 to Roe et al.; U.S. Pat. No. 5,569,234 issued Oct. 29, 1996 to Buell et al.; U.S. Pat. No. 5,580,411 issued Dec. 3, 1996 issued to Nease et al.; U.S. Pat. No. 5,653,703 issued Aug. 5, 1997 to Roe et al.; all of which are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A premoistened wipe comprising: a nonwoven fibrous substrate including from about 0.5 grams to 8 grams of liquid per gram of dry fiber in said substrate and from about 0.004% to 10% antimicrobial protease inhibitor by weight of dry fiber in said substrate wherein said antimicrobial protease inhibitor is an aromatic diamidine, said aromatic diamidine having the formula:

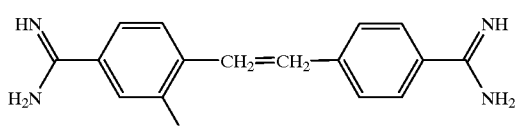

wherein X is H or OH, and

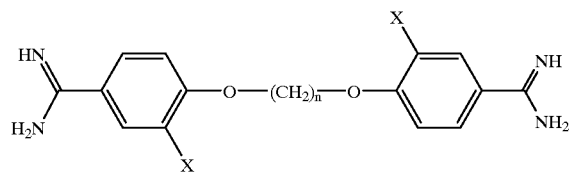

wherein n=3 to 12 and X is Cl, I, Br, F or H
wherein said aromatic diamidine is hexamidine diisethionate.

2. The premoistened wipe of claim 1 wherein said liquid includes a solvent comprising at least about 50% of said liquid by weight, wherein said solvent is oil, alcohol, water, and mixtures thereof and wherein said liquid further comprises from about 0.0005% to 10% hexamidine diisethionate by weight of said liquid.

3. A premoistened wipe comprising:
a nonwoven fibrous substrate including from about 0.5 grams to 8 grams of liquid per gram of dry fiber said liquid further comprising:
a) a solvent comprising at least about 50% of said liquid by weight, said solvent selected from the group consisting of oil, alcohol, water, and mixtures thereof; and
b) at least one Antimicrobial protease inhibitor comprising from about 0.0005% to 10% of said liquid by weight wherein said antimicrobial protease inhibitor is an aromatic diamidine said aromatic diamidine having the formula:

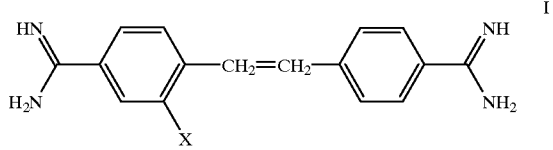

wherein X is H or OH, and

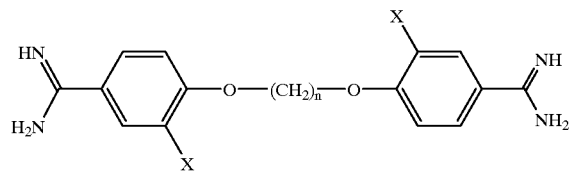

wherein n=3 to 12 and X is Cl, I, Br, F or H
wherein said aromatic diamidine is hexamidine diisethionate.

4. The premoistened wipe of claim 3 wherein said liquid further comprises:
a) an optional humectant(s) comprising from about 0.5% to 10% of said liquid by weight, said humectant(s) selected from the group consisting of glycerin, sorbitol, phospholipids, propylene glycol and mixtures thereof;
b) an optional emollient(s) comprising from about 0.1% to 10% of said liquid by weight, wherein said emollient(s) is selected from the group consisting of fatty acid esters, alkyl ethoxylates, fatty acid ester ethoxylates, fatty alcohols, polysiloxanes, mucopolysaccharides, or mixtures thereof;

c) an optional surfactant(s) comprising from about 0.01% to 10% of said liquid by weight, said surfactant(s) selected from the group consisting of nonionic surfactants, anionic surfactants, cationic surfactants, amphoteric surfactants, zwitterionic surfactants, and mixtures thereof; and d) an optional preservative(s) comprising from about 0.01% to 1% of said liquid by weight, said preservative(s) selected from the group consisting of methylparaben, propylparaben, and 2-Bromo-2-nitropropane-1,3 Diol, and mixtures thereof.

* * * * *

UNITED STATES PATENT AND TRADEMARK OFFICE
CERTIFICATE OF CORRECTION

PATENT NO. : 6,207,596 B1
DATED : March 27, 2001
INVENTOR(S) : Francis James Rourke et al.

It is certified that error appears in the above-identified patent and that said Letters Patent is hereby corrected as shown below:

Title page,
Item [75], Inventors, delete "Frederic," and insert therefore -- Fredric --.

Column 2,
Line 25, delete

"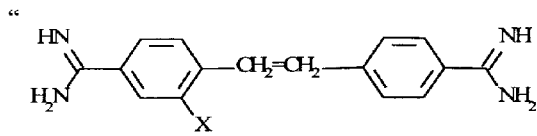            I and insert therefor
--
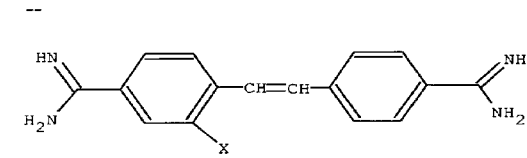            I

--.

Column 5,
Line 25, delete

"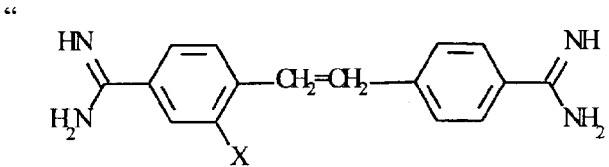            I and insert therefor
--
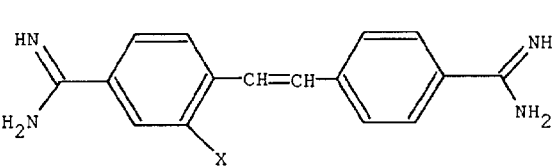            I

--.

Column 6,
Line 27, delete "Coming" and insert therefor -- Corning --.

UNITED STATES PATENT AND TRADEMARK OFFICE
CERTIFICATE OF CORRECTION

PATENT NO. : 6,207,596 B1  
DATED : March 27, 2001  
INVENTOR(S) : Francis James Rourke et al.

Page 2 of 3

It is certified that error appears in the above-identified patent and that said Letters Patent is hereby corrected as shown below:

Column 9,
Line 28, delete "microcuvetteis" and insert therefor -- microcuvette is --.
Line 53, delete "aliquotof" and insert therefor -- aliquot of --.

Column 10,
Line 37, delete "nitroanilideis" and insert therefor -- nitroanilide is --.

Column 11,
Line 41, delete "Method 1 a" and insert therefor -- Method 1a --.
Line 47, delete "Method 1 b" and insert therefor -- Method 1b --.

Column 13,
Line 62, delete

"
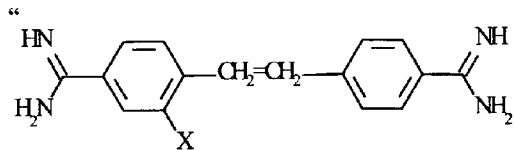

and insert therefor
--
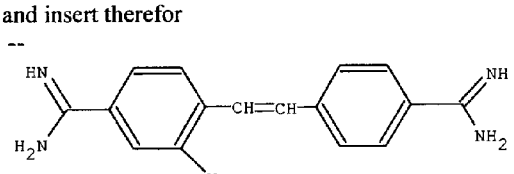

I

"

I

--.

UNITED STATES PATENT AND TRADEMARK OFFICE
CERTIFICATE OF CORRECTION

PATENT NO.   : 6,207,596 B1
DATED        : March 27, 2001
INVENTOR(S)  : Francis James Rourke et al.

It is certified that error appears in the above-identified patent and that said Letters Patent is hereby corrected as shown below:

<u>Column 14,</u>
Line 1, delete "and" and insert therefor -- or --.
Line 28, delete " b) at least one Antimicrobial" and insert therefor -- b) at least one antimicrobial --.
Line 41, delete "and" and insert therefor -- or --.

Signed and Sealed this

First Day of April, 2003

JAMES E. ROGAN
*Director of the United States Patent and Trademark Office*